United States Patent
Han et al.

(10) Patent No.: US 11,072,788 B2
(45) Date of Patent: Jul. 27, 2021

(54) EXPANSIN-AGARASE ENZYME COMPLEX AND METHOD FOR DEGRADING AGAR BY USING SAME

(71) Applicant: KOREA UNIVERSITY RESEARCH AND BUSINESS FOUNDATION, Seoul (KR)

(72) Inventors: Sung Ok Han, Seoul (KR); Da-woon Jeong, Seoul (KR); Jeong-Eun Hyeon, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 16/472,970

(22) PCT Filed: Jan. 2, 2018

(86) PCT No.: PCT/KR2018/000009
§ 371 (c)(1),
(2) Date: Jun. 24, 2019

(87) PCT Pub. No.: WO2018/124839
PCT Pub. Date: Jul. 5, 2018

(65) Prior Publication Data
US 2020/0190501 A1 Jun. 18, 2020

(30) Foreign Application Priority Data
Jan. 2, 2017 (KR) .................. 10-2017-0000152

(51) Int. Cl.
| | | |
|---|---|---|
| *C12N 9/42* | (2006.01) | |
| *C12N 9/90* | (2006.01) | |
| *C12P 19/14* | (2006.01) | |
| *C12N 9/96* | (2006.01) | |
| *C07K 14/32* | (2006.01) | |
| *C12N 9/38* | (2006.01) | |

(52) U.S. Cl.
CPC .............. *C12N 9/96* (2013.01); *C07K 14/32* (2013.01); *C12N 9/244* (2013.01); *C12N 9/2468* (2013.01); *C07K 2319/00* (2013.01); *C12Y 302/01006* (2013.01); *C12Y 302/01081* (2013.01)

(58) Field of Classification Search
CPC .... C12P 19/14; C12P 7/10; C12P 7/04; Y02E 50/10; C12N 9/2434; C12N 9/2445; C12N 15/81; C12N 9/90; C12Y 302/01021; C12Y 302/01081; C12Y 503/01004

USPC .................. 435/69.7, 209, 72, 254.11, 320.1
See application file for complete search history.

(56) References Cited

U.S. PATENT DOCUMENTS

2011/0151538 A1 6/2011 Bayer et al.
2011/0250668 A1 10/2011 Suzuki et al.

FOREIGN PATENT DOCUMENTS

JP      2010-252789 A    11/2010
KR  10-2012-0098247 A     9/2012

OTHER PUBLICATIONS

Devos et al., Proteins: Structure, Function and Genetics, 2000, vol. 41: 98-107.*
Witkowski et al., Biochemistry 38:11643-11650, 1999.*
Kisselev L., Structure, 2002, vol. 10: 8-9.*
Kim, Eun Sil et al., "Functional Characterization of a Bacterial Expansin From Bacillus subtilis for Enhanced Enzymatic Hydrolysis of Cellulose", *Biotechnology and bioengineering*, vol. 102, Issue 5, Apr. 1, 2009 (pp. 1342-1353).
Chen, Chao et al., "Integratation of bacterial expansin-like proteins into cellulosome promotes the cellulose degradation", Applied Microbiology and Biotechnology, vol. 100, Issue 6, 2016 (pp. 2203-2212).
Jeong Da Woon et al., "Integration of Bacterial Expansin on Agarolytic Complexes to Enhance the Degrading Activity of Red Algae by Control of Gelling Properties", Marine Biotechnology, vol. 20, No. 1, Nov. 18, 2017 (pp. 1-9).
International Search Report dated Apr. 11, 2018 in counterpart International Application No. PCT/KR2018/000009 (2 pages in English and 2 pages in Korean).
Korean Notice of Allowance dated Apr. 25, 2018 in counterpart Korean Patent Application No. 10-2017-0000152 (1 page in Korean).

\* cited by examiner

*Primary Examiner* — Robert B Mondesi
*Assistant Examiner* — Mohammad Y Meah
(74) *Attorney, Agent, or Firm* — NSIP Law (57) ABSTRACT

The present invention relates to an expansin-agarase enzyme complex and a method of degrading agar by using the same. The use of the enzyme complex according to the present invention can efficiently degrade agar obtained from marine biomass, and thus can efficiently provide not only galactose or glucose, necessary for ethanol production, but also useful biologically active substances, such as diose, triose, and oligosaccharides.

5 Claims, 5 Drawing Sheets
Specification includes a Sequence Listing.

EXPANSIN-AGARASE ENZYME COMPLEX AND METHOD FOR DEGRADING AGAR BY USING SAME

CROSS REFERENCE TO RELATED APPLICATIONS

This application is a U.S. National Stage Application of International Application No. PCT/KR2018/000009, filed on Jan. 2, 2018, which claims the benefit under 35 USC 119(a) and 365(b) of Korean Patent Application No. 10-2017-0000152, filed on Jan. 2, 2017, in the Korean Intellectual Property Office, the entire disclosure of which is incorporated herein by reference for all purposes.

TECHNICAL FIELD

The present invention relates to an expansin-agarase enzyme complex and a method of degrading agar using the same, and more particularly to an expansin-agarase enzyme complex in which a fusion protein of the dockerin module of cellulase and an expansin protein is assembled with a cohesin module-linked agarase via dockerin-cohesin interaction, and a method of degrading agar using the same.

BACKGROUND ART

In recent years, marine algae whose cell walls are composed of many fibers and various polysaccharides have attracted attention as new bioenergy sources. The countries that produce marine algae are mainly Asian countries, including Korea, Japan, China, and Indonesia. In these countries, the sea area in which marine algae can be cultivated is bigger than land. In addition, marine algae grow at a faster rate than wood and plant-based cellulose and have the effect of reducing greenhouse gases by absorbing carbon dioxide in the air through photosynthetic reactions. Furthermore, since the content of lignin in marine algae is low, it is possible to simplify the process of pretreating marine algae. In addition, about 60 to 95% of these large marine algae are moisture and more than 50% of the remaining components are carbohydrates, indicating that these marine algae have much potential as raw materials for biofuels.

Meanwhile, in Korea and Japan, cultivation of layer (mainly *Porphyra yezoensis*) among red algae is active, and red algae occupy more than half of marine algae that grow naturally in Korea. In addition, red algae are more broadly distributed than brown algae or green algae, grow naturally in an environment ranging from shallow water to deep water where light rays arrive. Thus, these red algae include a large number of species and thus are very excellent in terms of raw material supply and demand. In addition, red algae contain larger amounts of carbohydrates, that is, monosaccharides that can be converted to ethanol by microorganisms, than other algae, and thus have advantages in terms of energy conversion. Large marine algae have various types of polysaccharides and combinations depending on their species, and among them, red algae contain cellulose, which is a polysaccharide constituting the cell wall inner layer, agar and carrageenan, which are viscous polysaccharides having a sulfate group and found between the outer layer and the cells, and also xylan, mannan and the like.

In particular, the contents of agar and carrageenan which are representative of large marine algae are 28% and 24% respectively, and the content of cellulose is 3 to 16%, which is not so high. Agar, a representative by-product of red algae processing and extraction, is not a polysaccharide composed of a single type of sugar monomer, but a mixture of agarose (60 to 80%) which is a neutral polysaccharide and agaropectin (20 to 40%) which is an acidic polysaccharide. Agarose is either a polymer made up of the repeating unit of agarobiose which is a disaccharide consisting of alternating D-galactose and 3,6-anhydro-L-galactose (AG) units linked by β-1,4 bond, linked by α-1,3 bond or a polymer made up of the repeating unit of neoagarobiose, which is a disaccharide consisting of alternating D-galactose and 3,6-anhydro-L-galactose (AG) units linked by α-1,3 bond, linked by β-1,4 bond. Agaropectin has the same basic structure as that of agarose, but contains an acidic group such as a sulfate group, and thus has weak gelling ability, unlike agarose.

Therefore, when agar isolated purely from soils, mud flats, and internal organs of underwater animals is effectively degraded, galactose or glucose necessary for ethanol production can be produced, and degraded metabolites, such as dioses, trioses and oligosaccharides, which are produced in the degradation reaction, can also be used as useful physiologically active substances. So far, seaweed polysaccharides, such as agar and carrageenan, have been extracted from red algae by a processing method, such as alkali, acid or enzyme treatment, and have been widely used industrially as useful food and cosmetic additives and health food resources.

However, red algae are difficult to use as a substrate for biofuel production due to the complicated structure of red algae themselves, which is difficult to degrade, and the disposal of byproducts and wastes generated in a producing process of a useful product remains a problem.

Meanwhile, expansin does not act to produce reducing sugar by adsorbing and acting on plant cell walls, but it is probably presumed that expansin cleaves the hydrogen bond between cellulose units, and thus increases the flexibility of cell wall tissues, thereby increasing the accessibility of cellulase to cellulose. Thus, it is presumed that when expansin is used together with cellulase, it increases the activity of cellulose (Kim E S, Lee H J, Bang W G, Choi I G, Kim K H., Biotechnology and Bioengineering 102:1342-1353, 2009). Expansin is largely divided into alpha-expansin (EXPA) and beta-expansin (EXPB). It is known that alpha-expansin acts mainly on the cell walls of dicotyledonous plants, and beta-expansin acts well on the cell walls of herbaceous plants, and adsorbs to xylan rather than to cellulose.

Accordingly, the present inventors have made extensive efforts to develop an enzyme having high agar degradation efficiency by increasing the adsorptive ability of agarase (previously known as an agar-degrading enzyme) to agar. As a result, the present inventors have prepared an enzyme complex in which agarase and expansin are linked, and have found that the enzyme complex has a better ability to degrade agar than the agarase or expansin alone, thereby completing the present invention.

DISCLOSURE OF INVENTION

Technical Problem

It is an object of the present invention to provide an enzyme complex having an excellent ability to degrade agar.

Another object of the present invention is to provide a method for producing the enzyme complex.

Still another object of the present invention is to provide a method of degrading agar using the enzyme complex.

Technical Solution

To achieve the above objects, the present invention provides an expansin-agarase enzyme complex in which a fusion protein of the dockerin module of cellulase and an expansin protein is assembled with a cohesin module-linked agarase via dockerin-cohesin interaction.

The present invention also provides a method for producing the expansin-agarase enzyme complex, comprising the steps of: (a) preparing a fusion protein of the dockerin module of cellulase and an expansin protein; (b) preparing a cohesin module-linked agarase; and (c) mixing the fusion protein of the dockerin module of cellulase and the expansin protein, with the cohesin module-linked agarase, thereby preparing the enzyme complex by dockerin-cohesin interaction.

The present invention also provides a method of degrading agar using the expansin-agarase enzyme complex.

BRIEF DESCRIPTION OF THE DRAWINGS

FIG. 5a shows the results of measuring degradation activity using purified agar as a substrate; FIG. 5b shows the results of measuring degradation activity using agar extracted from *Gelidium amansii* (also known as *umutgasari*) as a substrate; and FIG. 5c shows the results of measuring degradation activity using *Gelidium amansii* itself as a substrate.

BEST MODE FOR CARRYING OUT THE INVENTION

In the present invention, an enzyme complex of an expansin from a *Bacillus* sp. strain and an agarase that degrades marine biomass was produced and used to degrade marine biomass. As a result, it was confirmed that the enzyme complex had an increased ability to degrade agar. In the present invention, the expansin-agarase enzyme complex was used to degrade marine biomass, that is, *Gelidium amansii* which is used as the raw material of agar, and it was confirmed that the degradation rate of the agar increased and that the mechanism of action of the expansin on the agar is caused by the change in rheological properties by hydrogen bonding.

Therefore, in one aspect, the present invention is directed to an expansin-agarase enzyme complex in which a fusion protein of the dockerin module of cellulase linked to an expansin protein is assembled with a cohesin module-linked agarase via dockerin-cohesin interaction.

The dockerin that can be used in the present invention may be derived from endo-beta-1,4-glucanase-B, endo-beta-1,4-xylanase-B, or exo-glucanase-S, and the expansin that can be used in the present invention may be derived from *Bacillus, Clostridium, Clavibacter, Pectobacterium*, or *Micromonospora*, but is not limited thereto.

In the present invention, the expansin protein may have an amino acid sequence set forth in SEQ ID NO: 1.

In one example of the present invention, a fusion fragment of a *Bacillus* sp.-derived expansin protein-encoding gene and the dockerin domain gene of cellulase was introduced into an *E. coli* expression vector and expressed, and as a result, it was confirmed that a fusion protein of expansin and the dockerin module was produced.

The cohesin module that can be used in the present invention may be a mini-cellulose-binding protein A (mCbpA), a *Clostridium thermocellulm*-derived mini-scaffold protein (mCipA), or a *Clostridium cellulolyticum*-derived mini-scaffold protein (mCipC), and the agarase that can be used in the present invention may be derived from *Pseudomonas, Saccharophagus*, or *Aleromonas*, but is not limited thereto.

In another example, a fusion fragment of the mini-cellulose-binding protein A (mCbpA) gene and an agarase-encoding gene was introduced into an *E. coli* expression vector and expressed.

In the present invention, the cohesin module may be a mini-cellulose-binding protein A (mCbpA), and the agarase may be beta-agarase.

In still another example, the fusion protein of the dockerin module and expansin was assembled with the cohesin module-linked agarase via dockerin-cohesin interaction, thereby producing an expansin-agarase enzyme complex.

Therefore, in another aspect, the present invention is directed to a method for producing the expansin-agarase enzyme complex, comprising the steps of: (a) preparing a fusion protein of the dockerin module of cellulase and an expansin protein; (b) preparing the cohesin module-linked agarase; and (c) mixing the fusion protein of the dockerin module of cellulase and the expansin protein, with the cohesin module-linked agarase, thereby preparing the enzyme complex by dockerin-cohesin interaction.

In another example of the present invention, an enzyme complex was prepared by assembling the dockerin-fused bacterial expansin protein BpEX-Doc with a chimeric beta-agarase protein derived from *Zobellia galactanivorans*, and the degradation activity of the enzyme complex was measured using purified agar, extracted agar and *Gelidium amansii* as substrates. As a result, it was confirmed that, for all the substrates, the enzyme complex showed higher degradation efficiency than the expansin or agarase alone.

Therefore, in still another aspect, the present invention is directed to a method of degrading agar using the expansin-agarase enzyme complex.

In the present invention, the agar may be purified agar, red algae-derived agar, or agar present in red algae.

Figure 5:
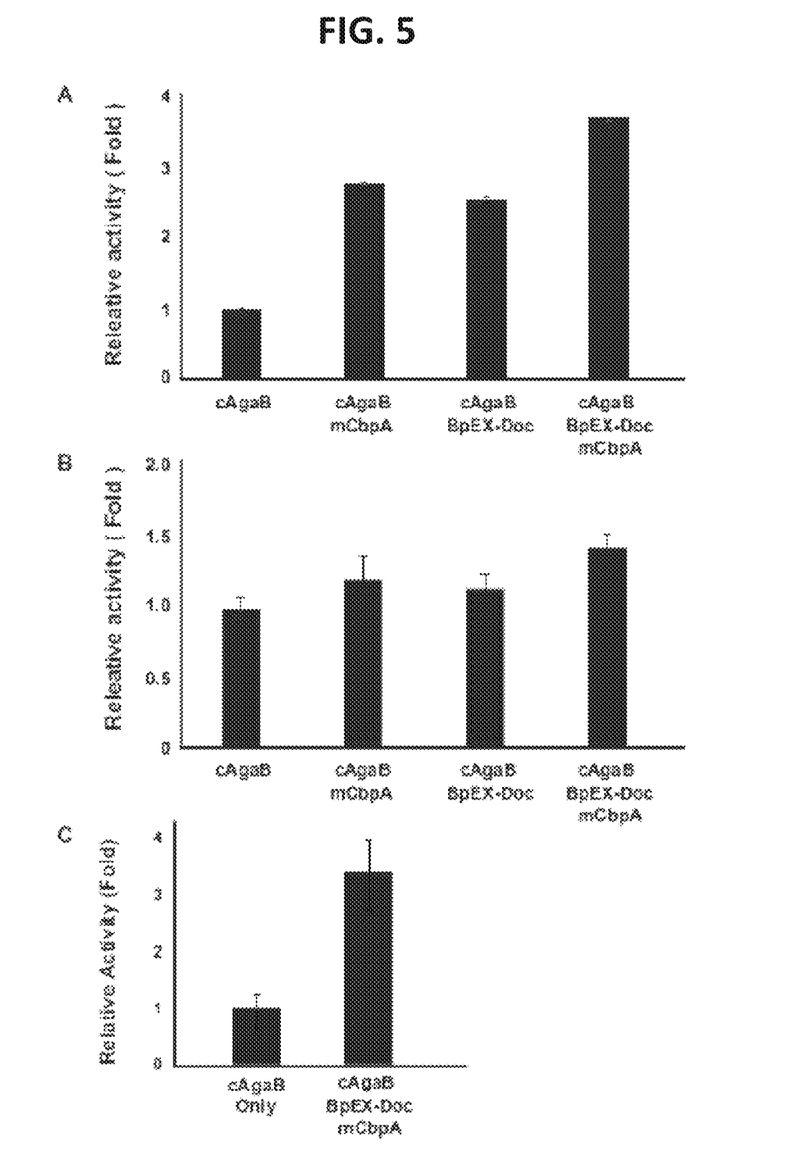
FIG. 5 shows the results of analyzing the activity of a complex obtained by assembling the dockerin-fused bacterial expansin protein BpEX-Doc presented in the present invention with a chimeric beta-agarase protein derived from *Zobellia galactanivorans* in order to demonstrate that the enzyme has increased degradation activity. Specifically.

In one example of the present invention, the degradation activities of agarase, an agarase-mCbpA fusion protein, a dockerin-expansin fusion protein and an expansin-agarase enzyme complex were analyzed using each of purified agar, agar extracted from *Gelidium amansii*, and *Gelidium amansii* itself as a substrate. As a result, it was confirmed that for all of the purified agar, the extracted agar and *Gelidium amansii* itself, the expansin-agarase enzyme complex showed higher degradation efficiency than the expansin or agarase alone (FIG. 5).

As used herein, the term "vector" refers to an expression vector capable of expressing a target protein in suitable host cells and to a genetic construct that includes essential regulatory elements to which a gene insert is operably linked in such a manner as to be expressed.

In general, a plasmid vector is an extrachromosomal cyclic double-stranded DNA and performs various functions in cells. It acts as an inhibitor that kills similar strains or species by producing antibiotic-resistant substances and bacteriocin, and performs biological functions, such as pigment production, compound decomposition and nitrogen fixing. It has a restriction enzyme site so that an exogenous DNA fragment having a length of up to about 10 kb can be inserted therein.

In order to overcome the possibility of inserting only a relatively small DNA fragment, which is a serious disadvantage of a plasmid vector and bacteriophage, cosmid which is an engineered hybrid of a plasmid and phase DNA may be used to clone a larger DNA fragment.

The vector has a cos site which is packaged into a phage particle, and also has a plasmid replication origin that replicates in a bacterial host, and a gene capable of selecting a plasmid. It is packaged into a protein envelope in a test tube, like a bacteriophage vector. However, after an *E. coli* host cell is infected with the packaged DNA, the DNA replicates as a plasmid rather than bacteriophage DNA, and is not lysed. It is 2.5 kb in size, and after it is packaged into a host cell by infection, the cos site has a size of 37 kb to 52 kb. After separation, it contains foreign DNA as an insert. In generally, one having a size of 35 kb to 45 kb may be cloned as a cosmid vector.

In addition, phage, a common type of bacteriophage vector, is derived from a 50-kb double-strand wild-type genome that has single-strand complementary ends of 12 nucleotides that can form base pairs, which are called cohesive termini or cos. Host cells are lysed in a lytic pathway after replication of a new virus and release of a progeny virus. This type of DNA may have 3 kb added to the total size of 52 kb, and may also contain only 5% of the genome. A vector providing a space for foreign DNA is free of nonessential DNA fragments.

A vector related to the present invention includes plasmid vectors (e.g., pSC101, ColE1, pBR322, pUC8/9, pHC79, and pUC19), cosmid vectors, bacteriophage vectors (e.g., gt4B, -Charon, z1 and M13), and viral vectors.

The viral vector includes a vector derived from retrovirus, for example, human immunodeficiency virus (HIV), murine leukemia virus (MLV), leukemia virus (e.g., avian sarcoma and leukosis virus, ASLV), spleen necrosis virus (SNV), Rous sarcoma virus (RSV), mouse mammary tumor virus 8 (MMTV), adenovirus, adeno-associated virus (AAV), and herpes simplex virus, but is not limited thereto.

As used herein, the term "operably linked" means that a nucleic acid expression control sequence is functionally linked to a nucleic acid sequence encoding the protein of interest so as to execute general functions. Operable linkage with the recombinant vector can be performed using a gene recombination technique well known in the art, and site-specific DNA cleavage and ligation can be performed using enzymes generally known in the art.

As used herein, the term "regulatory element" means an untranslated nucleic acid sequence that assists in, enhances, or otherwise affects the transcription, translation or expression of a nucleic acid sequence that encodes a protein. The expression vector of the present invention essentially includes a genetic circuit of the present invention as a regulatory element, and may include an expression regulatory element that can affect the expression of a protein, such as, for example, an initiation codon, a termination codon, a polyadenylation signal, an enhancer, or a signal sequence for membrane targeting or secretion.

A polyadenylation signal increases the stability of transcripts or facilitates cytosolic entry. An enhancer sequence is a nucleic acid sequence which is located at various sites in a promoter and increases transcriptional activity compared to the transcriptional activity of the promoter when the enhancer sequence is absent. Signal sequences include, but are not limited to, a PhoA signal sequence, an OmpA signal sequence, etc., when the host is an *Escherichia* sp. strain; an amylase signal sequence, a subtilisin signal sequence, etc., when the host is a *Bacillus* sp. strain; and a mating factor (MF) signal sequence, a SUC2 signal sequence, etc., when the host is yeast.

In addition, when being a replicable expression vector, the vector may include a replication origin, a specific nucleic acid sequence that initiates replication.

The vector according to the present invention may comprise a selection marker. The selection marker is used to select cells transformed with the vector. Here, markers giving selectable phenotypes, such as drug tolerance, auxotrophy, tolerance to cytotoxic agents, or expression of surface proteins, may be used as the selection marker. Since only the cells expressing the selection marker survive in an environment treated with a selective agent, it is possible to select the transformed cells. Representative examples of the selection marker include ura4, leu1, his3, etc., which are auxotrophic markers, but the types of markers that may be used in the present invention are not limited by the above examples.

In the present invention, "host cell" means a cell which parasitizes other microorganisms or genes and supply nutrients, and which is transformed with a vector that has various genetic or molecular effects in the host cell. In the competence state of receiving foreign DNA, foreign DNA such as a vector may be inserted into the host cell. When a vector is successfully introduced into the host cell, the genetic character of the vector is provided to the host cell.

Preferably, the host microorganisms of the present invention may be Gram-negative bacteria, which include a *Salmonella* sp. strain, an *Acinebacter* sp. strain, an *Escherichia* sp. strain, a *Pseudomonas* sp. strain, a *Klebsiella* sp, strain, etc. For example, the Gram-negative bacteria include *Salmonella typhimurium, Acinebacter calcoaceticus, E. coli, Pseudomonas aeruginosa, Klebsiella aerogenes, Acinebacter baumannii, Klebsiella pneumonia*, etc., but host cells that can be transformed with the vector of the present invention are not limited thereto.

As a method of introducing a vector into the host cell, a transformation method can be used. As used herein, the term "transformation" refers to a process of introducing DNA into a host cell and making the DNA replicable therein as a chromosomal factor or by completion of chromosomal integration, which is a phenomenon of artificially causing a genetic change by introducing exogenous DNA into a cell.

The method of transformation used in the present invention may be any transformation method, and it may be easily performed according to the conventional method used in the art. Examples of the commonly used transformation method may include a $CaCl_2$ precipitation method, the Hanahan method with improved efficiency using dimethyl sulfoxide (DMSO) as a reducing agent in the $CaCl_2$ precipitation method, electroporation, a $CaPO_4$ precipitation method, a protoplast fusion method, a stirring method using silicon carbide fiber, an agrobacteria-mediated transformation method, a transformation method using polyethylene glycol (PEG), dextran sulfate-, lipofectamine-, and dry/suppression-mediated transformations, etc. The method for transforming the plasmid according to the present invention is not limited to these methods, but any method for transformation commonly used in the art may be used without limitation.

In addition, the host cell transformed by the above method may be cultured through a culture method commonly used in the art, if necessary, and the culture medium and period that can be used in the present invention may be selected arbitrarily by a person of ordinary skill in the art, if necessary.

In the present invention, preferably, an *E. coli* strain transformed was cultured in LB (Luria Bertani) medium for 12 hours, and then further cultured for 2 hours to induce production of fluorescent proteins from recombinant genes. Various media that can be commonly used in the art can be applied to the medium.

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1: Amplification of Bacterial Expansin Protein Gene

In order to clone expansin proteins for inhibiting the gelation of agar and increasing the degradation efficiency of agar, with reference to the nucleotide sequence of a bacterial expansin (BpEX) gene from the gDNA of a *Bacillus* sp. strain, primers were designed and synthesized such that the restriction enzyme BamHI recognition sequence was inserted at the 5' end of the forward primer (SEQ ID NO: 3) and the restriction enzyme HindIII recognition sequence was inserted at the 5' end of the reverse primer (SEQ ID NO: 4). Next, using the synthesized primers, PCR was performed. As a result, a 664-bp PCR band containing a bacterial expansin (BpEX) gene (SEQ ID NO: 2) could be observed.

SEQ ID NO: 3: ATAT ggatcc a ttgagtttcgctgtgccaa
SEQ ID NO: 4: GCGC aagctt attaggaagctgaacattgcc Thereafter, the bacterial expansin (BpEX) gene was cleaved using BamHI and HindIII, and then ligated into the *E. coli* expression vector pET22b(+) which was then transformed into *E. coli* BL21. Then, the ligated recombinant plasmid DNA was isolated from the transformant. The recombinant vector was named pET22(+) BpEX. In addition, the *E. coli* transformant was named BL21/BpEX.

Example 2: Amplification of Dockerin-Fused Bacterial Expansin Protein Gene

In order to clone the dockerin domain gene of cellulase linked with expansin for forming an enzyme complex in which agarase and expansin are assembled, primers were designed and synthesized such that the restriction enzyme HindIII recognition sequence was inserted at the 5' end of the forward primer (SEQ ID NO: 5) with reference to the nucleotide sequence of the bacterial expansin (BpEX) gene from the gDNA of a *Bacillus* sp. Strain, and the N-terminal 10-bp sequence was inserted at the 5' end of the reverse primer (SEQ ID NO: 6) with reference to the nucleotide sequence of the dockerin domain of an endo-beta-1,4-glucanas-B gene derived from a *Clostridium cellulovorans* sp. strain. Next, using the synthesized primers, PCR was performed. As a result, a 673-bp PCR band containing a bacterial expansin (BpEX) gene could be observed.

In addition, with reference to the nucleotide sequence of the dockerin domain of the endo-beta-1,4-glucanas-B gene from the gDNA of *Clostridium cellulovorans*, primers were designed and synthesized such that the C-terminal 10-bp sequence of the bacterial expansin (BpEX) gene derived from a *Bacillus* sp. strain was inserted at the 5' end of the forward primer (SEQ ID NO: 7), and the restriction enzyme XhoI recognition sequence was inserted at the 5' end of the reverse primer (SEQ ID NO: 8). Next, using the synthesized primers, PCR was performed. As a result, a 211-bp PCR band containing a 211-bp dockerin domain gene (SEQ ID NO: 9) of the endo-beta-1,4-glucanase-B gene could be observed.

```
SEQ ID NO: 5:
GCGCAAGCTTTTGAGTTTCGCTGTGCCAA

SEQ ID NO: 6:
CAGCGATCCATTAGGAAGCTGAACATTGC

SEQ ID NO: 7:
GCTTCCTAATGGATCCGCTGGCTCC

SEQ ID NO: 8:
GCGCCTCGAGTAAAAGCATTTTTTTAAGAACAGCTAAAT
``` the nucleotide sequence of the dockerin domain of the endo-beta-1,4-glucanas-B gene

```
                                           (SEQ ID NO: 9)
Ggatccgctggctccgctgctggttctggggaattcgatgttaacaaaga tggaaaggtaaatgctatcgattatgcagtgcttaaatcaattcttttag gtacaaatactaacgttgatttatcagtatcagacatgaataaggatggt aaagtaaatgctttggatttagctgttcttaaaaaaatgctttta
```

C-terminal 10-bp sequence of dockerin domain of endo-beta-1,4-glucanas-B gene

```
SEQ ID NO: 10:
ggatccgctg
```

C-terminal 10-bp sequence of bacterial expansin (BpEX) gene

```
SEQ ID NO: 11:
gcttcctaat
```

The obtained amplification products of the bacterial expansin (BpEX) gene and the dockerin domain gene of cellulase were electrophoresed on 0.8% agarose gel, and DNA fragments on the agarose gel were recovered using a gel extraction kit (GeneAll).

Then, using the recovered DNA fragments, overlap PCR reaction was performed to ligate the dockerin domain gene of cellulase with the bacterial expansin (BpEX) gene. From the two recovered DNA fragments, primers were designed and synthesized such that the restriction enzyme HindIII was inserted at the 5' end of the forward primer (SEQ ID NO: 12) and the restriction enzyme XhoI recognition sequence was inserted at the 5' end of the reverse primer (SEQ ID NO: 13). PCR reaction was performed, and as a result, a 864-bp PCR band containing a fusion of the dockerin domain gene (SEQ ID NO: 14) of cellulase and the bacterial expansin (BpEX) gene could be observed.

Figure 1A:
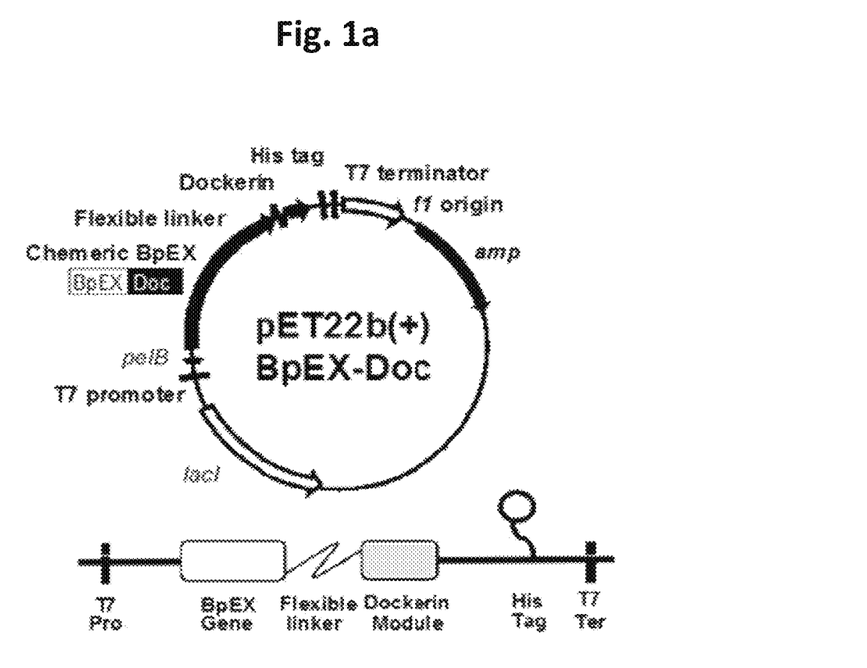
FIG. 1a is a schematic view of the recombinant vector pET22(+) BpEX-Doc inserted with the dockerin-fused bacterial expansin protein BpEX-Doc gene constructed through the design of a bacterial expansin protein gene derived from a *Bacillus* sp. strain, in accordance with the present invention.

Thereafter, the dockerin-fused bacterial expansin protein BpEX-Doc gene was cleaved using HindIII and XhoI, and then ligated into the *E. coli* expression vector pET22b(+) which was then transformed into *E. coli* BL21. Next, the ligated recombinant plasmid DNA was separated from the transformants. The recombinant vector was named pET22 (+) BpEX-Doc (FIG. 1a). Also, the *E. coli* transformant was named BL21/BpEX-Doc.

SEQ ID NO: 12:
GCGCAAGCTTTTGAGTTTCGCTGTGCCAA

SEQ ID NO: 13:
GCGCCTCGAGTAAAAGCATTTTTTTAAGAACAGCTAAAT

SEQ ID NO: 14:
Gatgttaacaaagatggaaaggtaaatgctatcgattatgcagtgcttaa atcaattcttttaggtacaaatactaacgttgatttatcagtatcagaca tgaataaggatggtaaagtaaatgctttggatttagctgttcttaaaaaa atgcttta

Example 3: Expression of Bacterial Expansin Protein and Dockerin-Fused Bacterial Expansin Protein BpEX-Doc in *E. coli* Transformant In order to examine the expression of enzyme proteins in the transformants obtained in Examples 1 and 2, His-tag purification and SDS-PAGE were performed.

Figure 1B:
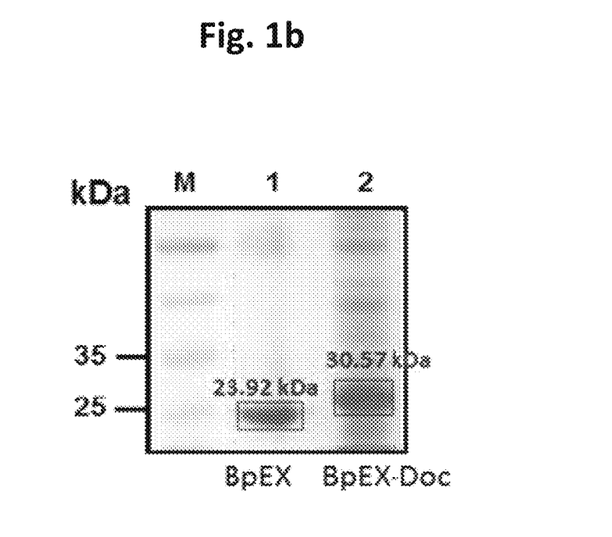
FIG. 1b shows the results of the expression of bacterial expansin protein in an *E. coli* strain inserted with the recombinant pET22(+) BpEX-Doc, before and after fusion of the protein with the dockerin.

The *E. coli* transformant was treated with IPTG to induce the expression of the bacterial expansin protein and dockerin-fused bacterial expansin protein, and then shake-cultured at 16° C. for 12 hours and centrifuged to collect the cells. Then, the cells were disrupted using ultrasonic waves and centrifuged, and the supernatant was concentrated (Millipore, amicon 10 kDa cut off) to obtain the corresponding proteins which were then loaded onto SDS-PAGE. Next, Western blot analysis was performed using a His-tag attached to the C-terminal end of each protein. As a result, it could be seen that the protein bands appeared at the expected sizes for the bacterial expansin protein and dockerin-fused bacterial expansin protein (FIG. 1b).

Example 4: Analysis of Cellulose-Binding Efficiency of Bacterial Expansin Protein and Dockerin-Fused Bacterial Expansin Protein in *E. coli* Transformant In order to analyze the cellulose-binding efficiency of the carbohydrate-binding module of each of the bacterial expansin protein and dockerin-fused bacterial expansin protein obtained in Example 3, binding assay was performed using phosphoric acid-swollen cellulose (PASC). The detailed experimental conditions are as follows:

Blocking Sample: 50 mg/mL bovine serum albumin (BSA), 25° C., 1 h
Protein Sample: Final concentration of 1 mg/mL, 4° C. for 10 min
Binding Buffer: 500 μL of binding buffer (50 mM sodium acetate, pH 5.0)
Wash Buffer: 50 mM sodium acetate, pH 5.0

Figure 2:
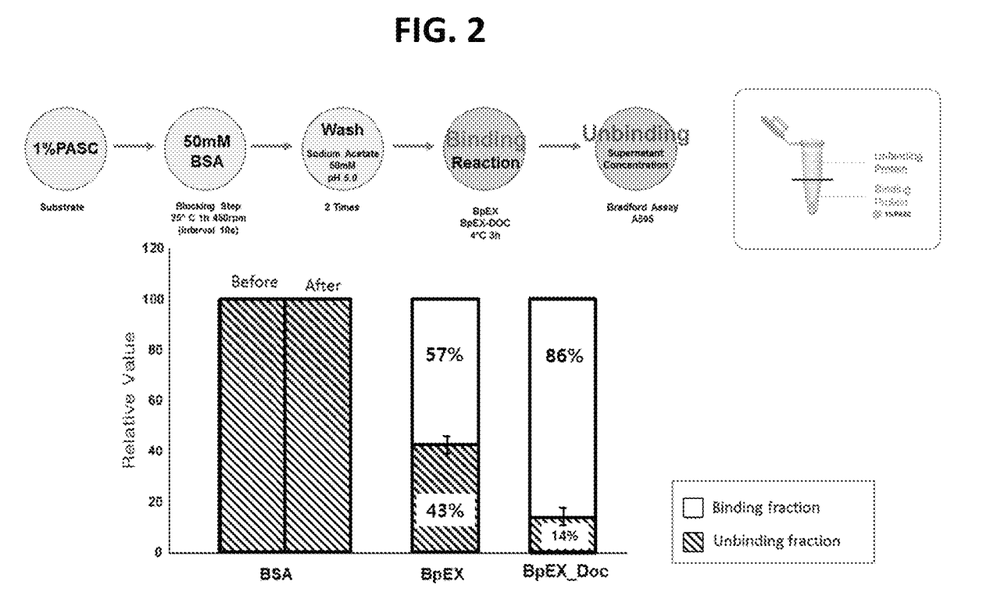
FIG. 2 shows the results of examining the cellulose-binding efficiency of BpEX-Doc, the bacterial expansin protein linked with the dockerin module of endo-beta-glucanase-B gene, using PASC as a substrate, in order to confirm the action of the carbohydrate binding module of the dockerin-fused bacterial expansin protein BpEX-Doc constructed in the present invention.

As a result, as shown in FIG. 2, it could be confirmed that the cellulose binding ability of the dockerin-fused expansin protein was significantly higher than that of the expansin protein.

Figure 3:
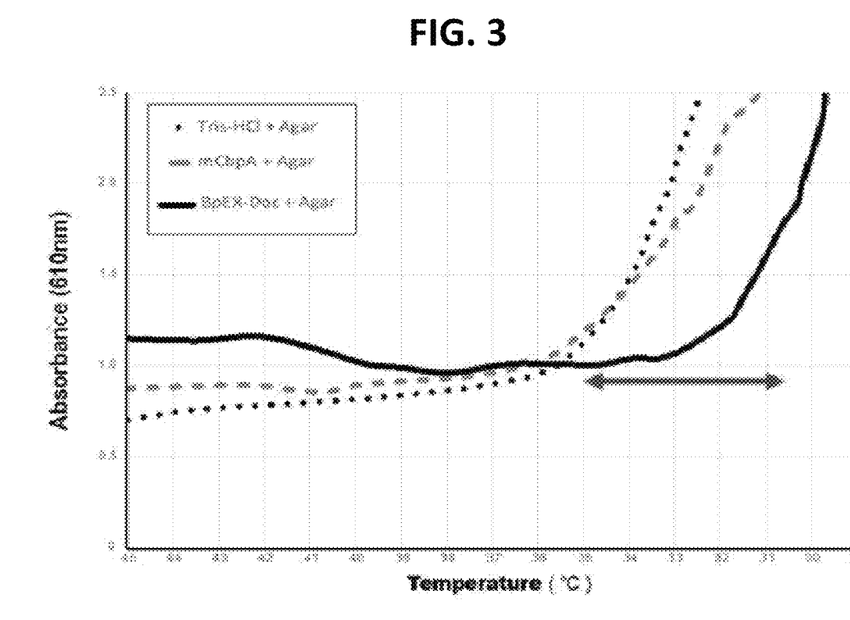
FIG. 3 shows the decrease of gelling temperature of agar in the presence of the protein BpEX-Doc by analyze the effect of the protein BpEX-Doc on the gelling temperature of agar using Lugol's solution.
Figure 4:
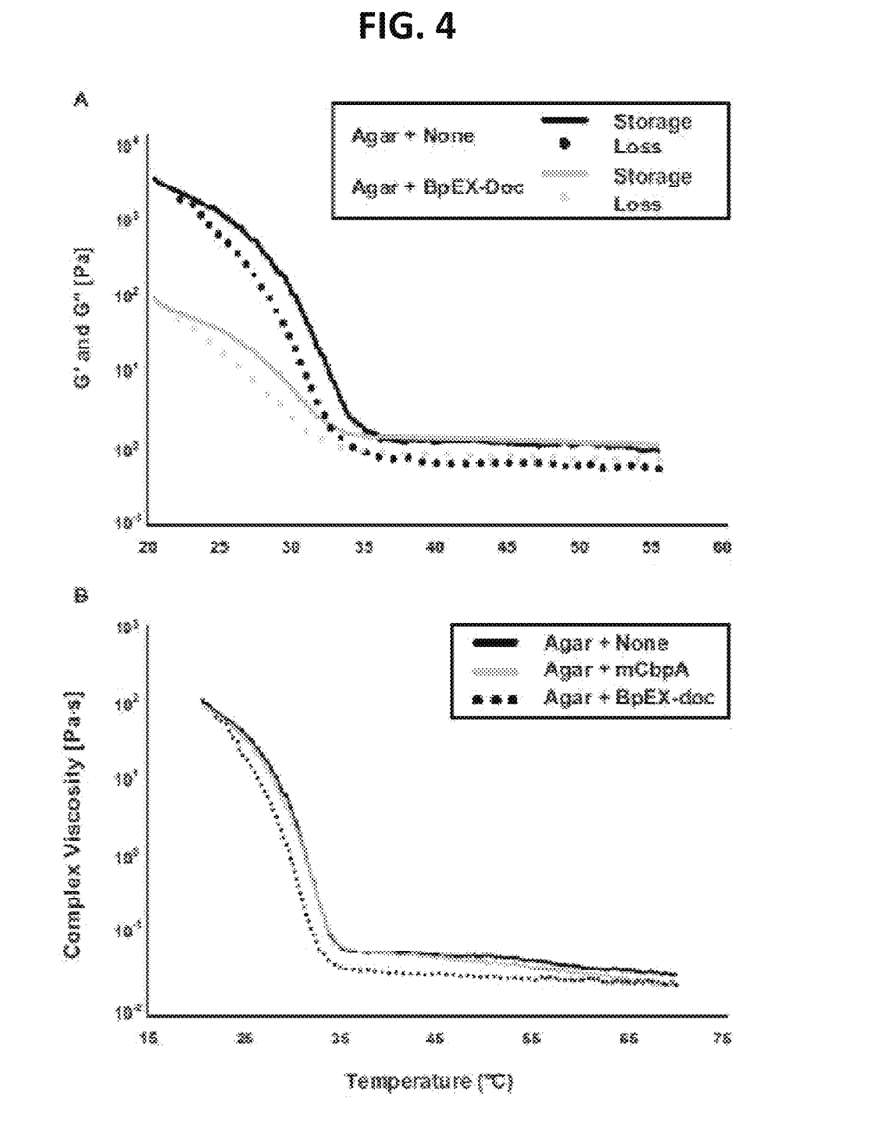
FIG. 4 shows the results of measuring temperature-dependent changes in the storage moduli and loss moduli of agar in the presence of the protein BpEX-Doc by a rheometer (FIG. 4a), and time-dependent changes in the viscosity of agar in the presence of the protein BpEX-Doc (FIG. 4b), in order to analyze the effect of the dockerin-fused bacterial expansin protein BpEX-Doc of the present invention on the time-dependent gelation of agar.

Example 5: Analysis of the Rheological Effect of Bacterial Expansin Protein on Agar Structure In order to analyze the effect of the bacterial expansin protein (obtained in Example 3) on the agar structure, analysis performed using a spectrometer and a rheometer. In the experiment using the spectrometer, whether the gelling temperature would decrease was measured using Lugol's solution as a stain reagent, and the results are shown in FIG. 3. In the experiment using the rheometer, temperature-dependent changes in the storage moduli and loss moduli of an agar substrate in the presence of the bacterial expansin protein were measured, and the results are shown in FIG. 4a. In addition, temperature-dependent changes in the viscosity of an agar substrate in the presence of the bacterial expansin protein were measured, and the results are shown in FIG. 4b. The detailed experimental conditions are as follows:

Steel parallel plate geometry: 25 mm radius
Conditions: 2% strain, 2° C./min rate, 5 Hz frequency, 2% strain amplitude

Example 6: Construction of Enzyme Complex of Bacterial Expansin Protein and Beta-Agarase and Analysis of its Activity for Various Agar Substrates In order to clone a mini-cellulose-binding protein A having a cellulose binding module (CBM) and two cohesin modules in the cellulose-binding protein A which is a primary scaffolding subunit derived from *Clostridium cellulovorans*, with reference to the nucleotide sequence, primers were synthesized such that the restriction enzyme BamHI recognition sequence (ggatcc) was inserted at the 5' end of the forward primer (SEQ ID NO: 15) and the restriction enzyme XhoI recognition sequence (ctcgag) was inserted at the 5' end of the reverse primer (SEQ ID NO: 16). As a result, a 1659-bp PCR band containing a mCbpA gene (SEQ ID NO: 17), a portion of the cellulose-binding protein-A gene derived from *Clostridium cellulovorans*, could be observed.

SEQ ID NO: 15:
ggatccgcagcgacatcatcaa

SEQ ID NO: 16:
GCGCctcgaggctataggatctccaatatttat

Next, the mini-cellulose-binding protein-A mCbpA gene was cleaved using BamHI and XhoI, and then ligated into the *E. coli* expression vector pET22b(+) which was then transformed into *E. coli* BL21. Then, the ligated recombinant plasmid DNA was separated from the transformant. The recombinant vector was named pET22b-mCbpA and is shown in FIG. 2. In addition, the *E. coli* transformant was named BL21/mCbpA.

In order to clone the dockerin domain gene of cellulase for dockerin-fused agarase, primers were designed and synthesized such that the restriction enzyme SacI recognition sequence was inserted at the 5' end of the forward primer (SEQ ID NO: 18) with reference to the nucleotide sequence of the beta-agarase AgaB gene from the genomic DNA of a Zobellia sp. Strain, and the N-terminal 10-bp sequence was inserted at the 5' end of the reverse primer (SEQ ID NO: 19) with reference to the nucleotide sequence of the dockerin domain of the endo-beta-1,4-glucanas-B gene from the gDNA of a Clostridium cellulovorans sp. strain. Next, using the synthesized primers, PCR was performed. As a result, a 1005-bp PCR band containing beta-agarase could be observed.

SEQ ID NO: 18:
GCGCGAGCTCCGGCGACAATTCAAAATTTGATA

SEQ ID NO: 19:
CAGCGGATCCTTTCTCTACAGGTTTATAGATC

In addition, with reference to the nucleotide sequence of the dockerin domain of the endo-beta-1,4-glucanas-B gene from the gDNA of Clostridium cellulovorans, primers were designed and synthesized such that the C-terminal 10-bp sequence of the beta-agarase AgaB gene from the genomic DNA of a Zobellia sp. strain was inserted at the 5' end of the forward primer (SEQ ID NO: 22) and the restriction enzyme NotI recognition sequence was inserted at the 5' end of the reverse primer (SEQ ID NO: 23). Next, using the synthesized primers, PCR was performed. As a result, a 211-bp PCR band containing a dockerin domain gene (SEQ ID NO: 24) of the endo-beta-1,4-glucanas-B gene could be observed.

SEQ ID NO: 22:
TGTAGAGAAAGGATCCGCTGGCTCCG

SEQ ID NO: 23:
GCGCGGCCGCTCAATGATGATGATGATGATGTAAAAGCATTTTTTTAAG

SEQ ID NO: 24:
ggatccgctggctccgctgctggttctggggaattcgatgttaacaaaga tggaaaggtaaatgctatcgattatgcagtgcttaaatcaattcttttag gtacaaatactaacgttgatttatcagtatcagacatgaataaggatggt aaagtaaatgctttggatttagctgttcttaaaaaaatgcttta The obtained amplification products of the beta-agarase AgaB gene and the dockerin domain gene of cellulase were electrophoresed on 0.8% agarose gel, and DNA fragments on the agarose gel were recovered using a gel extraction kit (GeneAll).

Next, in order to link the beta-agarase AgaB gene with the dockerin domain gene of cellulase, overlap PCR reaction was performed using the recovered DNA fragments. From the two recovered DNA fragments, primers were designed and synthesized such that the restriction enzyme SacI recognition sequence was inserted at the 5' end of the forward primer (SEQ ID NO: 25) and the restriction enzyme NotI recognition sequence was inserted at the 5' end of the reverse primer (SEQ ID NO: 26). PCR reaction was performed, and as a result, a 1225-bp PCR band containing a chimeric fusion protein of the dockerin domain gene (SEQ ID NO: 14) of cellulase and the beta-agarase AgaB gene derived from Zobellia galactanivorans could be observed.

Thereafter, the AgaB Doc gene which is the dockerin-fused chimeric beta-agarase AgaB gene was cleaved using SacI and NotI, and then ligated into the E. coli expression vector pET22b(+) which was then transformed into E. coli BL21. Then, the ligated recombinant plasmid DNA was isolated from the transformant. The recombinant vector was named pET22(+) AgaB-Doc. In addition, the E. coli transformant was named BL21/AgaB-Doc.

SEQ ID NO: 25:
GCGCGAGCTCCGGCGACAATTCAAAATTTGATA

SEQ ID NO: 26:
GCGCGGCCGCTCAATGATGATGATGATGATGTAAAAGCATTTTTTAAG

The recombinant strains BL21/mCbpA and BL21/AgaB-Doc ware treated with IPTG to induce the expression of the bacterial expansin protein and dockerin-fused bacterial expansin protein, and then shake-cultured at 16° C. for 12 hours and centrifuged to collect the cells. Then, the cells were disrupted using ultrasonic waves and centrifuged, and the supernatant was concentrated (Millipore, amicon 10 kDa cut off) to obtain the corresponding proteins which were then used in a further experiment.

In order to confirm that a complex is formed by linkage between the bacterial expansin protein linked with the dockerin module of the endo-beta-1,4-glucanase-B gene and the beta-agarase protein linked with the dockerin module of the endo-beta-1,4-glucanase-B gene via interaction with the mini-cellulose-binding protein mCbpA, the two proteins were mixed at a predetermined ratio and incubated, and then formation of the complex was induced.

In order to demonstrate that the bacterial expansin protein linked with the dockerin module of the endo-beta-1,4-glucanase-B gene and the beta-agarase protein linked with the dockerin module of the endo-beta-1,4-glucanase-B gene form a complex by binding with the mini-cellulose-binding protein mCbpA, whether the activity of the beta-agarase would increase was measured. The degradation activity of each of agarase, a mixed enzyme of agarase-expansin, and a mixed enzyme of agarase-expansin-mCbpA was measured using purified agar as a substrate, and as a result, it could be seen that the degradation activity increased in the order of agarase, agarase-expansin, and agarase-expansin-mCbpA (FIG. 5). Here, since mCbpA is an inactive protein having no degradation activity, it can be demonstrated that the increased activity results from enzyme complex formation.

In order to more specifically confirm the activity of the resulting complex, the activity of each of agarase, an agarase-mCbpA fusion protein, a dockerin-expansin fusion protein and an expansin-agarase enzyme complex was analyzed using various agars (purified agar, agar extracted from Gelidium amansii, and Gelidium amansii itself) as substrates.

As a result, as shown in FIG. 5, the expansin-agarase enzyme complex showed higher degradation activity than the expansin or agarase alone for all the purified agar, the extracted agar and Gelidium amansii itself.

INDUSTRIAL APPLICABILITY

The use of the enzyme complex according to the present invention can efficiently degrade agar obtained from marine biomass, and thus can efficiently provide not only galactose or glucose necessary for ethanol production, but also useful biologically active substances, such as dioses, trioses, and oligosaccharides.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. An expansin-agarase enzyme complex comprising: a fusion protein comprising an expansin having the amino acid sequence set forth in SEQ ID NO: 1 linked with a dockerin module of a cellulase: and an agarase encoded by the nucleotide sequence set forth in SEQ ID NO: 20 linked with a cohesin module;
   wherein the expansin-agarase enzyme complex comprising the fusion protein comprising the expansin and the agarase linked with the cohesin module is assembled via interaction of the dockerin-cohesin interaction of the dockerin module and the cohesin module; and
   wherein the expansin-agarase enzyme complex has agar degrading activity.

2. The enzyme complex of claim 1, wherein the dockerin module is obtained from endo-beta-1,4-glucanase-B.

3. The enzyme complex of claim 1, wherein the cohesin module is a mini-cellulose-binding protein A (mCbpA).

4. A method of degrading agar using the expansin-agarase enzyme complex of claim 1.

5. The method of claim 4, wherein the agar is purified agar, red algae-derived agar, agar present in red algae.

* * * * *

SEQUENCE LISTING

<160> NUMBER OF SEQ ID NOS: 26

<210> SEQ ID NO 1
<211> LENGTH: 219
<212> TYPE: PRT
<213> ORGANISM: Artificial Sequence
<220> FEATURE:
<223> OTHER INFORMATION: Expansin from Bacillus sp.

<400> SEQUENCE: 1

```
Leu Ser Phe Ala Val Pro Asn Met Lys Ala Ala Ser Val Leu Asp Glu
1               5                   10                  15

Val Arg Glu Ser Tyr Ala Thr Tyr Thr Gly Ser Gly Tyr Ser Gly Gly
            20                  25                  30

Ala Ala Leu Leu Asp Pro Ile Pro Ser Asp Met Lys Ile Thr Ala Leu
        35                  40                  45

Asn Pro His Asp Tyr Asn Tyr Lys Gly Ile Asn Ala Ala Leu Ala Gly
    50                  55                  60

Ala Tyr Leu Glu Val Lys Gly Pro Lys Gly Lys Thr Val Val Tyr Val
65                  70                  75                  80

Thr Asp Lys Tyr Pro Glu Gly Ala Lys Gly Ala Leu Asp Leu Ser His
                85                  90                  95

Asn Ala Phe Ala Lys Ile Gly Asn Met Ala Asp Gly Lys Ile Pro Ile
            100                 105                 110

Ser Trp Lys Ile Val Lys Ala Pro Ile Ser Gly Asn Val Val Tyr Arg
        115                 120                 125

Ile Lys Glu Gly Ser Ser Lys Trp Trp Ala Ala Ile Gln Val Arg Asn
    130                 135                 140

His Lys Tyr Pro Ile Met Lys Met Glu Tyr Tyr Lys Asp Gly Gln Trp
145                 150                 155                 160

Val Asn Met Glu Lys Thr Asp Tyr Asn His Phe Leu Gly Phe Asn Met
                165                 170                 175

Gly Ser Lys Ser Leu Pro Val Arg Ile Thr Asp Ile Arg Gly Val Ile
            180                 185                 190

Val Lys Asp Lys Leu Pro Ala Leu Pro Ser Thr Ala Ala Ser Gln Ala
        195                 200                 205

Tyr Thr Val Lys Gly Asn Val Gln Leu Pro Asn
    210                 215
```

<210> SEQ ID NO 2
<211> LENGTH: 664
<212> TYPE: DNA
<213> ORGANISM: Artificial Sequence
<220> FEATURE:
<223> OTHER INFORMATION: Expansin from Bacillus sp.

<400> SEQUENCE: 2

```
gatccattga gtttcgctgt gccaaacatg aaagcggcat ctgtccttga tgaagtacga      60
gaaagctatg caacttatac gggatctggt tactcagggg gcgccgcatt attagatcct     120
attccatctg acatgaaaat tacggcttta aatccccatg actataacta taagggata     180 aatgcggcac ttgcaggggc ttaccttgaa gtaaagggtc aaaaggaaa aaccgttgtg     240 tatgtaaccg ataaatatcc agaaggagcg aaggagctc ttgatctttc tcataatgcc     300
tttgccaaaa tcggcaatat ggcagatggg aaaatcccaa ttagttggaa aattgtaaaa     360
gcaccgatta gcggaaatgt agtttacaga ataaagaag gtagcagtaa gtggtgggct     420
gcgattcaag tgcgcaatca taaatatccg attatgaaaa tggaatatta caaagatgga     480
```

```
caatgggtga acatggaaaa gacagactac aaccatttcc ttggatttaa tatggggtct    540
aaatctcttc ctgttcgaat cacagatatc cgcggggtca tcgtaaagga taaattaccc    600
gctcttccat ctactgctgc ttcacaggcc tatactgtaa aaggcaatgt tcagcttcct    660
aata                                                                 664
```

<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3

```
atatggatcc attgagtttc gctgtgccaa                                      30
```

<210> SEQ ID NO 4
<211> LENGTH: 31
<212> TYPE: DNA
<213> ORGANISM: Artificial Sequence
<220> FEATURE:
<223> OTHER INFORMATION: primer

<400> SEQUENCE: 4

```
gcgcaagctt attaggaagc tgaacattgc c                                    31
```

<210> SEQ ID NO 5
<211> LENGTH: 29
<212> TYPE: DNA
<213> ORGANISM: Artificial Sequence
<220> FEATURE:
<223> OTHER INFORMATION: primer

<400> SEQUENCE: 5

```
gcgcaagctt ttgagtttcg ctgtgccaa                                       29
```

<210> SEQ ID NO 6
<211> LENGTH: 29
<212> TYPE: DNA
<213> ORGANISM: Artificial Sequence
<220> FEATURE:
<223> OTHER INFORMATION: primer

<400> SEQUENCE: 6

```
cagcgatcca ttaggaagct gaacattgc                                       29
```

<210> SEQ ID NO 7
<211> LENGTH: 25
<212> TYPE: DNA
<213> ORGANISM: Artificial Sequence
<220> FEATURE:
<223> OTHER INFORMATION: primer

<400> SEQUENCE: 7

```
gcttcctaat ggatccgctg gctcc                                           25
```

<210> SEQ ID NO 8
<211> LENGTH: 39
<212> TYPE: DNA
<213> ORGANISM: Artificial Sequence
<220> FEATURE:
<223> OTHER INFORMATION: primer

<400> SEQUENCE: 8

```
gcgcctcgag taaaagcatt tttttaagaa cagctaaat                           39

<210> SEQ ID NO 9
<211> LENGTH: 195
<212> TYPE: DNA
<213> ORGANISM: Artificial Sequence
<220> FEATURE:
<223> OTHER INFORMATION: endo-beta-glucanase-B

<400> SEQUENCE: 9
ggatccgctg gctccgctgc tggttctggg gaattcgatg ttaacaaaga tggaaaggta    60
aatgctatcg attatgcagt gcttaaatca attcttttag gtacaaatac taacgttgat   120
ttatcagtat cagacatgaa taaggatggt aaagtaaatg ctttggattt agctgttctt   180
aaaaaaatgc tttta                                                    195

<210> SEQ ID NO 10
<211> LENGTH: 10
<212> TYPE: DNA
<213> ORGANISM: Artificial Sequence
<220> FEATURE:
<223> OTHER INFORMATION: N-termial of endo-beta-glucanase-B gene

<400> SEQUENCE: 10
ggatccgctg                                                           10

<210> SEQ ID NO 11
<211> LENGTH: 10
<212> TYPE: DNA
<213> ORGANISM: Artificial Sequence
<220> FEATURE:
<223> OTHER INFORMATION: C-terminal of BpEX

<400> SEQUENCE: 11
gcttcctaat                                                           10

<210> SEQ ID NO 12
<211> LENGTH: 29
<212> TYPE: DNA
<213> ORGANISM: Artificial Sequence
<220> FEATURE:
<223> OTHER INFORMATION: primer

<400> SEQUENCE: 12
gcgcaagctt ttgagtttcg ctgtgccaa                                      29

<210> SEQ ID NO 13
<211> LENGTH: 39
<212> TYPE: DNA
<213> ORGANISM: Artificial Sequence
<220> FEATURE:
<223> OTHER INFORMATION: primer

<400> SEQUENCE: 13
gcgcctcgag taaaagcatt tttttaagaa cagctaaat                           39

<210> SEQ ID NO 14
<211> LENGTH: 159
<212> TYPE: DNA
<213> ORGANISM: Artificial Sequence
<220> FEATURE:
<223> OTHER INFORMATION: dockerin domain

<400> SEQUENCE: 14
gatgttaaca aagatggaaa ggtaaatgct atcgattatg cagtgcttaa atcaattctt    60
```

| | | |
|---|---|---|
| ttaggtacaa atactaacgt tgatttatca gtatcagaca tgaataagga tggtaaagta | 120 | |
| aatgctttgg atttagctgt tcttaaaaaa atgctttta | 159 | |

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15

| | |
|---|---|
| ggatccgcag cgacatcatc aa | 22 |

<210> SEQ ID NO 16
<211> LENGTH: 33
<212> TYPE: DNA
<213> ORGANISM: Artificial Sequence
<220> FEATURE:
<223> OTHER INFORMATION: primer

<400> SEQUENCE: 16

| | |
|---|---|
| gcgcctcgag gctataggat ctccaatatt tat | 33 |

<210> SEQ ID NO 17
<211> LENGTH: 1647
<212> TYPE: DNA
<213> ORGANISM: Artificial Sequence
<220> FEATURE:
<223> OTHER INFORMATION: mCbpA gene

<400> SEQUENCE: 17

| | |
|---|---|
| gcagcgacat catcaatgtc agttgaattt acaactctca acaaatcagc acaaacaaac | 60 |
| tcaattacac caataatcaa aattactaac acatctgaca gtgatttaaa tttaaatgac | 120 |
| gtaaaagtta gatattatta cacaagtgat ggtacacaag acaaactttt ctggtgtgac | 180 |
| catgctggtg cattattagg aaatagctat gttgataaca ctagcaaagt gacagcaaac | 240 |
| ttcgttaaag aaacagcaag cccaacatca acctatgata catatgttga atttggattt | 300 |
| gcaagcggag cagctactct taaaaaagga caatttataa ctattcaagg aagaataaca | 360 |
| aaatcagact ggtcaaacta cactcaaaca aatgactatt catttgatgc aagtagttca | 420 |
| acaccagttg taaatccaaa agttacagga tatataggtg gagctaaagt acttggtaca | 480 |
| gcaccaggtc cagatgtacc atcttcaata attaatccta cttctgcaac atttgataaa | 540 |
| aatgtaacta acaagcaga tgttaaaact actatgactt taaatggtaa cacatttaaa | 600 |
| acaattacag atgcaaacgg tacagctcta aatgcaagca ctgattatag tgtttctgga | 660 |
| aatgatgtaa caataagcaa agcttattta gcaaaacaat cagtaggaac aactacatta | 720 |
| aactttaact ttagtgcagg aaatcctcaa aaattagtaa ttacagtagt tgacacacca | 780 |
| gttgaagctg taacagctac aattggaaaa gtacaagtaa atgctggaga acggtagca | 840 |
| gtaccagtta acttaacaaa agttccagca gctggtttag caacaattga attaccatta | 900 |
| acttttgatt ctgcatcatt agaagtagta tcaataactg ctggagatat cgtattaaat | 960 |
| ccatcagtaa acttctcttc tacagtaagt ggaagcacaa taaattatt attcttagat | 1020 |
| gatacattag gaagccaatt aatcactaag gatggagttt ttgcaacaat aacatttaaa | 1080 |
| gcaaaagcta taactggaac aactgcaaaa gtaacttcag ttaaattagc tggaacacca | 1140 |
| gtagttggtg atgcgcaatt acaagaaaaa ccttgtgcag ttaacccagg aacagtaact | 1200 |

| | |
|---|---:|
| atcaatccaa tcgataatag aatgcaaatt tcagttggaa cagcaacagt aaaagctgga | 1260 |
| gaaatagcag cagtgccagt aacattaaca agtgttccat caactggaat agcaactgct | 1320 |
| gaagcacaag taagttttga tgcaacatta ttagaagtag catcagtaac tgctggagat | 1380 |
| atcgtattaa atccaacagt aaacttctct tatacagtaa acggaaatgt aataaaatta | 1440 |
| ttattcctag atgatacatt aggaagccaa ttaattagta aagatggagt tttgtaaca | 1500 |
| ataaacttca aagcaaaagc tgtaacaagc acagtaacaa caccagttac agtatcagga | 1560 |
| acacctgtat ttgcagatgg tacattagca gaagtacaat ctaaaacagc agcaggtagc | 1620 |
| gttacaataa atattggaga tcctata | 1647 |

<210> SEQ ID NO 18
<211> LENGTH: 33
<212> TYPE: DNA
<213> ORGANISM: Artificial Sequence
<220> FEATURE:
<223> OTHER INFORMATION: primer

<400> SEQUENCE: 18

| | |
|---|---:|
| gcgcgagctc cggcgacaat tcaaaatttg ata | 33 |

<210> SEQ ID NO 19
<211> LENGTH: 33
<212> TYPE: DNA
<213> ORGANISM: Artificial Sequence
<220> FEATURE:
<223> OTHER INFORMATION: primer

<400> SEQUENCE: 19

| | |
|---|---:|
| gcgcgagctc cggcgacaat tcaaaatttg ata | 33 |

<210> SEQ ID NO 20
<211> LENGTH: 1005
<212> TYPE: DNA
<213> ORGANISM: Artificial Sequence
<220> FEATURE:
<223> OTHER INFORMATION: AgaB gene

<400> SEQUENCE: 20

| | |
|---|---:|
| ggcgacaatt caaaatttga tagtgcaacg gatttgccgg ttgaacaaga acaagaacag | 60 |
| gaaacggaac aagagggaga acccgaagaa agttcggagc aagaccttgt cgaggaggtc | 120 |
| gattggaagg atattcccgt acccgccgat gcaggaccga atatgaagtg ggagtttcaa | 180 |
| gagatttccg ataattttga atatgaggcc cctgcggata taaggggag tgaatttctc | 240 |
| gaaaagtggg acgattttta tcacaatgcc tgggcaggcc cagggctgac cgaatggaaa | 300 |
| cgggacaggt cctatgtagc cgatggcgag ctaaagatgt gggcgacaag aaaaccgggc | 360 |
| tccgataaaa taaacatggg gtgcattact tctaagaccc gagtggtcta tcctgtttat | 420 |
| attgaagcaa gggcaaaggt catgaactct accttggctt cggatgtttg gctcttaagt | 480 |
| gccgatgaca cccaagagat agatattcta gaggcatatg gggccgatta ttccgaaagt | 540 |
| gccggaaagg atcattccta tttttctaaa aaggtacaca taagccatca cgtctttatt | 600 |
| cgagacccat ttcaagatta tcaaccaaag gatgccggtt cttggttcga agacggcacc | 660 |
| gtctggaaca aagagttcca taggtttggt gtgtattgga gggatccatg gcatctagaa | 720 |
| tattacatag acggtgttct ggtgaggacc gtttcgggaa aggacattat cgaccccaaa | 780 |
| cactttacga atacaacgga tcccggtaat acggaaatcg atacccgcac cggtctcaat | 840 |
| aaagaaatgg atattattat caatacagaa gaccaaactt ggcggtcttc accggcctcg | 900 |

```
ggtttacagt ctaataccta tacgccaacg gacaatgaat tgagcaatat agaaaacaat    960
acgttcgggg tcgattggat caggatctat aaacctgtag agaaa                   1005
```

<210> SEQ ID NO 21
<211> LENGTH: 335
<212> TYPE: PRT
<213> ORGANISM: Artificial Sequence
<220> FEATURE:
<223> OTHER INFORMATION: beta-agarase

<400> SEQUENCE: 21

```
Gly Asp Asn Ser Lys Phe Asp Ser Ala Thr Asp Leu Pro Val Glu Gln
1               5                   10                  15

Glu Gln Glu Gln Glu Thr Glu Gln Gly Glu Pro Glu Glu Ser Ser
            20                  25                  30

Glu Gln Asp Leu Val Glu Glu Val Asp Trp Lys Asp Ile Pro Val Pro
        35                  40                  45

Ala Asp Ala Gly Pro Asn Met Lys Trp Glu Phe Gln Glu Ile Ser Asp
    50                  55                  60

Asn Phe Glu Tyr Glu Ala Pro Ala Asp Asn Lys Gly Ser Glu Phe Leu
65                  70                  75                  80

Glu Lys Trp Asp Asp Phe Tyr His Asn Ala Trp Ala Gly Pro Gly Leu
                85                  90                  95

Thr Glu Trp Lys Arg Asp Arg Ser Tyr Val Ala Asp Gly Glu Leu Lys
            100                 105                 110

Met Trp Ala Thr Arg Lys Pro Gly Ser Asp Lys Ile Asn Met Gly Cys
        115                 120                 125

Ile Thr Ser Lys Thr Arg Val Val Tyr Pro Val Tyr Ile Glu Ala Arg
    130                 135                 140

Ala Lys Val Met Asn Ser Thr Leu Ala Ser Asp Val Trp Leu Leu Ser
145                 150                 155                 160

Ala Asp Asp Thr Gln Glu Ile Asp Ile Leu Glu Ala Tyr Gly Ala Asp
                165                 170                 175

Tyr Ser Glu Ser Ala Gly Lys Asp His Ser Tyr Phe Ser Lys Lys Val
            180                 185                 190

His Ile Ser His His Val Phe Ile Arg Asp Pro Phe Gln Asp Tyr Gln
        195                 200                 205

Pro Lys Asp Ala Gly Ser Trp Phe Glu Asp Gly Thr Val Trp Asn Lys
    210                 215                 220

Glu Phe His Arg Phe Gly Val Tyr Trp Arg Asp Pro Trp His Leu Glu
225                 230                 235                 240

Tyr Tyr Ile Asp Gly Val Leu Val Arg Thr Val Ser Gly Lys Asp Ile
                245                 250                 255

Ile Asp Pro Lys His Phe Thr Asn Thr Thr Asp Pro Gly Asn Thr Glu
            260                 265                 270

Ile Asp Thr Arg Thr Gly Leu Asn Lys Glu Met Asp Ile Ile Asn
        275                 280                 285

Thr Glu Asp Gln Thr Trp Arg Ser Ser Pro Ala Ser Gly Leu Gln Ser
    290                 295                 300

Asn Thr Tyr Thr Pro Thr Asp Asn Glu Leu Ser Asn Ile Glu Asn Asn
305                 310                 315                 320

Thr Phe Gly Val Asp Trp Ile Arg Ile Tyr Lys Pro Val Glu Lys
                325                 330                 335
```

```
<210> SEQ ID NO 22
<211> LENGTH: 26
<212> TYPE: DNA
<213> ORGANISM: Artificial Sequence
<220> FEATURE:
<223> OTHER INFORMATION: primer

<400> SEQUENCE: 22
tgtagagaaa ggatccgctg gctccg                                         26

<210> SEQ ID NO 23
<211> LENGTH: 49
<212> TYPE: DNA
<213> ORGANISM: Artificial Sequence
<220> FEATURE:
<223> OTHER INFORMATION: primer

<400> SEQUENCE: 23
gcgcggccgc tcaatgatga tgatgatgat gtaaaagcat tttttttaag               49

<210> SEQ ID NO 24
<211> LENGTH: 195
<212> TYPE: DNA
<213> ORGANISM: Artificial Sequence
<220> FEATURE:
<223> OTHER INFORMATION: dockerin domain of endo-beta-1,4-glucanase-B
      gene

<400> SEQUENCE: 24
ggatccgctg gctccgctgc tggttctggg gaattcgatg ttaacaaaga tggaaaggta    60
aatgctatcg attatgcagt gcttaaatca attcttttag gtacaaatac taacgttgat   120
ttatcagtat cagacatgaa taaggatggt aaagtaaatg ctttggattt agctgttctt   180
aaaaaaatgc tttta                                                    195

<210> SEQ ID NO 25
<211> LENGTH: 33
<212> TYPE: DNA
<213> ORGANISM: Artificial Sequence
<220> FEATURE:
<223> OTHER INFORMATION: primer

<400> SEQUENCE: 25
gcgcgagctc cggcgacaat tcaaaatttg ata                                 33

<210> SEQ ID NO 26
<211> LENGTH: 49
<212> TYPE: DNA
<213> ORGANISM: Artificial Sequence
<220> FEATURE:
<223> OTHER INFORMATION: primer

<400> SEQUENCE: 26
gcgcggccgc tcaatgatga tgatgatgat gtaaaagcat tttttttaag               49
```